United States Patent [19]
Chung et al.

[11] Patent Number: 5,837,852
[45] Date of Patent: Nov. 17, 1998

[54] CAPPED NUCLEIC ACID OLIGOMERS THAT INHIBIT CAP-DEPENDENT TRANSCRIPTION OF THE INFLUENZA VIRUS ENDONUCLEASE

[75] Inventors: Thomas D. Y. Chung, Lambertville, N.J.; Christopher W. Cianci, Morrisville, Pa.; Moira Hagen; Mark Krystal, both of Cranbury, N.J.; Richard J. Colonno, Buckingham, Pa.

[73] Assignee: Bristol-Myers Squibb Company, Princeton, N.J.

[21] Appl. No.: 136,214

[22] Filed: Oct. 14, 1993

[51] Int. Cl.$^6$ ............................ C12N 5/00; C12N 15/00; C07N 14/00; A61K 48/00
[52] U.S. Cl. ................... 536/24.5; 536/23.1; 536/24.1; 536/24.3; 514/44
[58] Field of Search ................... 514/44; 536/27–29, 536/22.1, 23.1; 435/91.1, 91.31, 172.3, 320.1

[56] References Cited

U.S. PATENT DOCUMENTS

| | | | |
|---|---|---|---|
| 4,689,320 | 8/1987 | Kaji | 514/44 |
| 5,194,428 | 3/1993 | Agrawal et al. | 514/44 |

FOREIGN PATENT DOCUMENTS

| | | | |
|---|---|---|---|
| 0081099 | 6/1983 | European Pat. Off. | C07H 21/00 |

OTHER PUBLICATIONS

Technical Report No. 2, Antivirals Inc., pp. 1–16, Mar. 1993.
I. Ulmanen et al., Proc. Natl. Acad. Sci., USA, vol. 8, No. 12, pp. 7355–7359, 1981.
R. M. Krug et al., Proc. Natl. Acad. Sci., USA, vol. 77, No. 10, pp. 5874–5878, 1980.
E. Wagner et al., Nucleic Acids Research, vol. 19, No. 21, pp 5965–5971, 1991.
E. Rapaport et al. Proc. Natl. Acad. Sci., USA, vol. 72, No. 1, pp. 314–317, 1975.
E. Barbosa et al., The Journal of Biological Chemistry, vol. 253, No. 21, pp. 7698–7702, 1978.
S. A. Martin et al., The Journal of Biological Chemistry, vol. 250, No. 24, pp. 9330–9335, 1975.
S. J. Plotch et al., Cell, vol. 23, pp. 847–858, 1981.
S. J. Plotch et al., Proc. Natl. Acad. Sci., USA, vol. 76, No. 4, pp. 1618–1622, 1979.
M. Bouloy et al., Proc. Natl. Acad. Sci., USA, vol. 77, No. 7, pp. 3952–3956, 1980.
K. Kawakami et al., J. Biochem., vol. 89, No. 6, pp. 1759–1768, 1981.
A. Honda et al., The Journal of Biological Chemistry, vol. 261, No. 13, pp. 5987–5991, 1986.
A. R. Beaton et al., Nucleic Acids Research, vol. 9, No. 17, pp. 4423–4436, 1981.
M. Bouloy et al., Proc. Natl. Acad. Sci. USA, vol. 75, No. 10, pp. 4886–4890, 1978.
M. W. Shaw et al., Virus Research, vol. 1, pp. 455–467, 1984.
S. Martin et al., The Journal of Biological Chemistry, vol. 250, No. 24, pp. 9322–9329, 1975.
Marshall, Science, 269, 1995, 1050–1055.
Wu–Pong, Pharmaceutical Technology, 18, 1994, 102–114.
Rojanasa, Adv. Drug Del. Reviews, 18, 1996, 115–131.
Antivirals Inc., Technical Report #2, "Morpholino–type Neu–Genes™: The Next Generation of Antisense". Mar. 1993, pp. 1–16.
Stein, C.A. et al. "Antisense Oligonucleotides as Therapeutic Agents: Is the Bullet Really Magical?", Science 261: 1004–1011 (1993).
Leiter, J. et al. "Inhibition of Influenza Virus Replication by Phosphorothioate Oligodeoxynucleotides", PNAS 87: 3430–3434 (1990).
Bouloy, M. et al. "Both the 7–methyl . . . ", PNAS 77(7):3952–3956 (1980).
Krug, R.M. et al. "Priming and Inhibitory Activities . . . ", PNAS 77(10): 5874–5898 (1980).
Plotch, S.J. et al. "A Unique Cap (m$^7$GpppXm)–dependent influenza virion endonuclease . . . ", Cell 23: 847–858 (1981).

Primary Examiner—Jasemine C. Chambers
Assistant Examiner—Andrew Milne
Attorney, Agent, or Firm—Timothy J. Gaul

[57] ABSTRACT

Novel capped oligonucleotides useful in treatment of influenza infection. A synthetically derived 67-nucleotide RNA substrate, containing a [$^{32}$P] labeled cap-1 structure was used to analyze parameters of influenza virus endonuclease activity. This substrate was specifically cleaved by the influenza virus polymerase to yield a single capped 11-nucleotide fragment capable of directly priming transcription. An analysis of systematic truncations of this RNA substrate in cleavage, elongation, and binding reactions demonstrated that the minimum chain length required for cleavage was one nucleotide past the cleavage site. In contrast, the minimum chain length required for priming activity was found to be 9 nucleotides, while a chain length of at least 4 nucleotides was required for efficient binding. Based on these chain length requirements, the present inventors show that a pool of capped oligonucleotides—too short to prime transcription but long enough to bind with high affinity to the viral polymerase—are potent inhibitors of cap-dependent in vitro transcription.

14 Claims, 6 Drawing Sheets

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: mRNA ( x i ) SEQUENCE DESCRIPTION: SEQ ID NO:1:

GAAUACUCAA GCUAUG 16

( 2 ) INFORMATION FOR SEQ ID NO:2:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: mRNA ( x i ) SEQUENCE DESCRIPTION: SEQ ID NO:2:

GAAUACUCAA GCUAU 15

( 2 ) INFORMATION FOR SEQ ID NO:3:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: mRNA ( x i ) SEQUENCE DESCRIPTION: SEQ ID NO:3:

GAAUACUCAA GCUA 14

( 2 ) INFORMATION FOR SEQ ID NO:4:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: mRNA ( x i ) SEQUENCE DESCRIPTION: SEQ ID NO:4:

GAAUACUCAA GCU 13

( 2 ) INFORMATION FOR SEQ ID NO:5:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: mRNA ( x i ) SEQUENCE DESCRIPTION: SEQ ID NO:5:

GAAUACUCAA G            11

(2) INFORMATION FOR SEQ ID NO:6:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: mRNA (xi) SEQUENCE DESCRIPTION: SEQ ID NO:6:

GAAUACUCAA GC            12

(2) INFORMATION FOR SEQ ID NO:7:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: mRNA (xi) SEQUENCE DESCRIPTION: SEQ ID NO:7:

GAAUACUCAA            10

(2) INFORMATION FOR SEQ ID NO:8:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: mRNA (xi) SEQUENCE DESCRIPTION: SEQ ID NO:8:

GAAUACUCAA GCUAUNNNNN NNNNNNNNNN NNNNNNNNNN NNNNNNNNNN NNNNNNN            57

CAPPED NUCLEIC ACID OLIGOMERS THAT INHIBIT CAP-DEPENDENT TRANSCRIPTION OF THE INFLUENZA VIRUS ENDONUCLEASE

FIELD OF THE INVENTION

This invention relates to RNA oligomers, anti-viral agents, and to methods of treatment and prevention of influenza virus infection.

BACKGROUND OF THE INVENTION

Influenza A virus is a segmented, negative-stranded RNA virus which encodes its own RNA-dependent RNA polymerase. The polymerase is found as a complex of three proteins (PB1, PB2, and PA) at the 3' termini of nucleoprotein (NP)-encapsidated viral genome segments. Although the multiple steps involved in virus replication have been elucidated, knowledge of specific function and properties of the viral polymerase is lacking.

The first step of viral replication is transcription of mRNA from genome vRNA. This step is initiated by a "scavenging" of nascent host cell mRNA transcripts by the influenza polymerase complex. These cellular transcripts possess a "cap-1" structure ($m^7$GpppXm) at their 5' ends. These transcripts are first bound and then cleaved by the viral polymerase 9–15 nucleotides from their 5' ends, preferentially after purine residues, yielding primers for viral transcription (for a review, see reference 1). The high-affinity binding of these capped RNAs is mediated by the PB2 subunit of the viral polymerase (2,3). This overall process of capped RNA binding, cleavage, and elongation from primer fragments results in the production of chimeric viral mRNAs that contain host-derived heterogeneous sequences at their 5' ends (4,5).

This endonuclease reaction has been demonstrated in vitro(6–10) by incubating virus or viral cores with several eukaryotic mRNAs containing the cap-1 structure (α or β-globin mRNA), or with plant virus RNAs (AIMV or BMV) in which the cap-0 (m7GpppX) structures were enzymatically converted to cap-1 (m7GpppXm) structures. (For a description of the cap-1, cap-0 and other cap structures, see reference 22, pages 164–165, which is incorporated herein by reference.) Endonuclease activity was shown to be strictly dependent upon the presence of the 7-methyl group on the guanyl cap ($m^7$G) but could be further stimulated by additional O-methylation of the 2'-ribosyl hydroxyl group (3,11).

In the absence of added ribonucleotides or $Mg^{2+}$, the binding step can be isolated from other steps of transcription in vitro. One experimental approach employed a co-sedimentation analysis of cap-1 AIMV RNA with viral cores through glycerol gradients (3). In that analysis, a capped AIMV of 7 nucleotides ($m^7$GpppGmUUUUUAp) co-sedimented efficiently, while a cap-1 dinucleotide ($m^7$GpppGm) and trinucleotide ($m^7$GpppGmUp) did not. These results suggest that high affinity binding requires a chain length of between 3 and 7 nucleotides and a 5' cap.

To further define the contribution of the cap and RNA components, the present inventors developed the filter binding assay described herein. This assay measures radiolabeled VSV mRNA binding (completely cap-1) to viral cores entrapped on a nitrocellulose membrane.

SUMMARY OF THE INVENTION

In accordance with the present invention are novel compounds of the formula:

$$R—N^1—N^2—N^3—N^a—R^1 \quad\quad 1$$

and pharmaceutically acceptable salts thereof, wherein:

R is

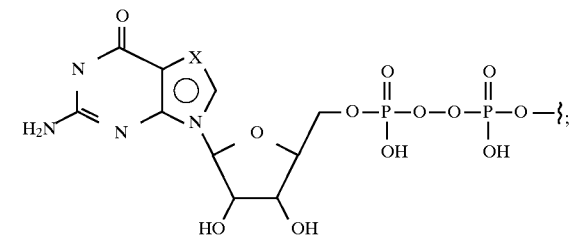

X is N or

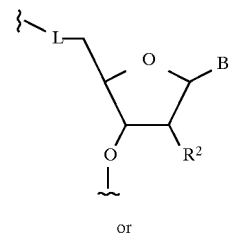

$N^a$ is $—N^4$, $—N^4—N^5$, $—N^4—N^5—N^6$, $—N^4—N^5—N^6—N^7$, or $—N^4—N^5—N^6—N^7—N^8$, $—N^4—N^5—N^6—N^7—N^8—N^9$, $—N^4—N^5—N^6—N^7—N^8—N^9—N^{10}$, or $—N^4—N^5—N^6—N^7—N^8—N^9—N^{10}—N^{11}$;

$N^1, N^2, N^3, N^4, N^5, N^6, N^7, N^8, N^9, N^{10}$, and $N^{11}$ are each independently

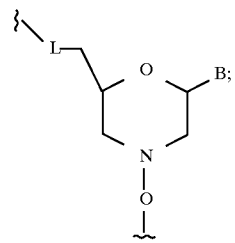

B is adenine, cytosine, guanine, thymine (provided $R^2$ is hydrogen), uracil (provided $R^2$ is hydroxy or methoxy), 6-methyladenine, 5-methylcytosine, or 2-methylguanine;

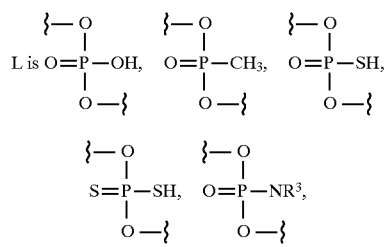

or

-continued

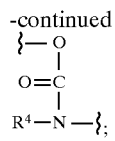

$R^1$ is hydrogen or

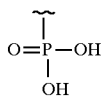

provided that $R^1$ is

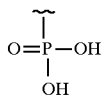

when $N^a$ is $-N^4-N^5-N^6-N^7-N^8-N^9-N^{10}$ or $-N^4-N5-N^6-N^7-N^8-N^9-N^{10}-N^{11}$;

$R^2$ is hydrogen for each of $N^1$ to $N^{11}$ or hydroxy or methoxy for each of $N^1$ to $N^{11}$;

$R^3$ is alkyl of 1 to 4 carbon atoms; and $R^4$ is hydrogen or methyl.

$N^1$ to $N^{11}$ are preferred to be adenylate, guanylate, uridylate, or cytidylate. $N^1$, $N^2$, $N^3$, and Na are preferred to be the nucleotides listed in Table 1.

The inventors discovered that oligomers of 4 to 8 nucleotides attached to an $m^7G$ cap bind with relatively high affinity to the viral polymerase but are not further cleaved to yield fragments that efficiently prime transcription. In addition, the inventors discovered that 3'-phosphorylated oligomers of up to 11 nucleotides are not dephosphorylated or elongated by the viral polymerase. Such capped oligomers are, therefore, inhibitors of primary influenza transcription and are useful as anti-influenza agents.

DETAILED DESCRIPTION OF THE INVENTION

Structural analysis: nucleotides ($N^1-N^2-N^3-N^a-R^1$)

Previous studies concerning the influenza virus endonuclease centered around the use of natural mRNA substrates. Although informative, no systematic study of the RNA chain lengths requirements of each of the three separate steps of binding, cleavage, and elongation was done.

Binding requirements

This work employed a novel capped and methylated 67-nucleotide RNA substrate. Whereas previously examined mRNA substrates exhibit several cleavage products (6,8), this novel substrate yields a single capped 11-nucleotide fragment having a 3' hydroxyl group. This single cleavage product could serve directly as a primer for elongation. The minimum chain length required for efficient binding of this capped substrate is 4 nucleotides (see Table 1). This further extends the lower limit of 7 nucleotides determined by Ulmanen et al. (3) for effective binding.

Cleavage requirements

Cleavage of this substrate requires as little as one base past the endonucleolytic site. Nuclease-treated substrates of various sizes were gel-purified, dephosphorylated if necessary, and examined in the absence of nucleotides to determine endonucleolytic cleavage. Endonucleolytic cleavage was only observed with substrates two bases past the specific G11 cleavage site. However, when a 12-base substrate was gel-purified from a mutant generated at the C12 position (C12→G), cleavage to an 11-base primer resulted (Table 1). These results indicate that the viral endonuclease requires only one nucleotide past the cleavage site.

Elongation requirements

The foregoing nuclease-treated, gel-purified substrates were also examined in the presence of nucleotides to determine priming of transcription.

Figure 2A:
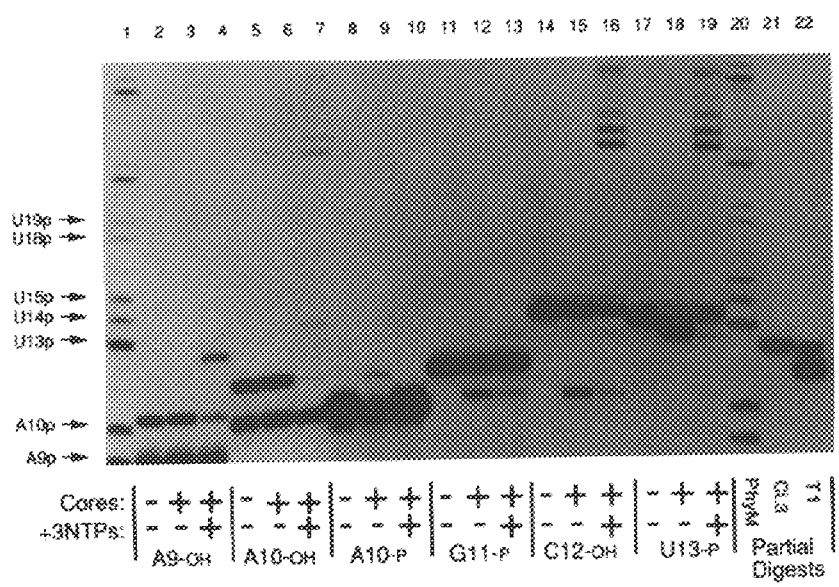
FIG. 2A–B shows chain length requirements for cleavage and priming activity of the RNA substrate. (A) 5'-Radiolabeled and capped fragments were generated by partial or complete digests with commercial RNAses, dephosphorylated by the reverse reaction of T4 polynucleotide kinase, purified and isolated by 20% PAGE/7M urea, and incubated with or without viral cores in the absence or presence of the three nucleotide triphosphates, ATP, CTP, and GTP (3 NTPs) as indicated. For the A9-OH and Al 10-OH fragments (lanes 2–7), the partial dephosphorylation reactions were used directly in elongation reactions. Sequencing ladders from partial RNAse digests of the capped 67-nucleotide substrate with PhyM (lane 1 and 20) are indicated on the left of the autoradiogram. Migration of the G11p and C12p fragments resulting from CL3 and T1RNAse digests (lanes 21 and 22) are indicated on the right. (B) Similar incubation of the 5'-radiolabeled, 3'-phosphorylated, capped C12-P fragment. Positions of secondary cleavage fragments are indicated on the right. Elongation products are indicated as in FIG. 1.

Capped RNA substrates with chains of 10, 11 and 12 nucleotides (and 3' OH) were able to prime transcription directly, without further cleavage. Of the RNA substrates shorter than 11 nucleotides, only the 9- and 10-nucleotide substrates exhibited any priming activity, suggesting that for this oligomer, 9 nucleotides is the minimum length required for initiation of transcription (FIG. 2). However, the 9 nucleotide primer only induces an aborted elongation product.

The 9–12 nucleotide length required for priming is similar to the previously observed 9–15 heterogeneous nucleotide length transferred to viral mRNA in vivo (4,5,33,34) and in vitro (6,8,35). The lack of priming by shorter fragments may thus result from insufficient chain length to span between the PB2 cap-binding site and the 3' end of the vRNA proximal to the cleavage or elongation sites.

In vivo (4,5,34) and in vitro (36) analyses also showed a marked preference for cleavage after purines among transcriptional primers (4,5). This preference is also reflected in the data obtained with the substrate and its derivatives.

An additional novel finding is that the viral polymerase lacks 3'-phosphatase activity. A purified G11-p fragment was not converted to the G11-OH fragment and was thus unable to efficiently prime transcription. When priming is inhibited by presence of this 3' phosphate, however, additional cleavage products not generally seen with this substrate can be generated (FIG. 2, lanes 12, 13). These additional cleavage products are also too short to prime transcription.

Structural analysis: cap portion (R)

The cap-binding reaction of capped RNA substrate to the influenza viral endonuclease is conveniently isolated from successive steps of in vitro transcription by omitting $Mg^{2+}$ and rNTPs. The polymerase-capped RNA complexes remain stably associated after binding to nitrocellulose filters or while pelleting through glycerol cushions.

The ribonucleotide component appears more significant than cap methylation states for high affinity binding between capped RNAs and the polymerase. Rabbit globin mRNA (cap-1), BMV RNA 4 (cap-0), and "core" capped VSV mRNA (cap-(-1)) all inhibited binding of radiolabeled cap-1 VSV mRNA equally well. In fact, uncapped ribopolymers of 100–200 nucleotides inhibit transcription in nanomolar dosage (36,37) with specificity for the endonuclease reaction (10). The potency of these uncapped RNAs increased with decreasing secondary structure, which may explain the lack of inhibitory binding by the more highly structured 5S RNA and tRNAs used as uncapped controls in our studies. The role of the cap structure may become more significant when secondary structure is introduced into an RNA or when it becomes very short. For example, binding of the RNA cap could aid in melting out secondary structure or in locking in the 5' terminus of the bound RNA.

The uncapped 100–200 nt ribopolymers (36, 37) are 11- to 50 times longer than the 4–9 nt capped oligonucleotides examined in this invention. Therefore, on a per nucleotide basis, 5' capping significantly increases affinity for binding and inhibitory potency.

The present inventors have also shown that neither the cap structure nor short ribonucleotide chain alone are sufficient to inhibit transcription. A capped dinucleotide, a complete Ti digest of 5S rRNA, and a decapped globin mRNA all failed to be potent inhibitors (Table 2).

Preparation and formulation

When $N^1$ to $N^{11}$ are

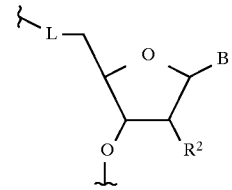

compounds of formula I may be synthesized by run-off in vitro transcription from engineered plasmid DNA of any sequence inserted downstream of known RNA polymerase promoters, followed by enzymatic capping if necessary as described in Materials and Methods below. Other compounds of formula I may be prepared by chemical methods known in the art. See, for example, references 38, 39, and 40.

Compound I is pictured as an acid and would lack hydrogen ions at physiological pH (e.g., from the phosphate groups defined by R). For pharmaceutical use, compound I may be formulated as a salt with sodium, lithium, potassium, or ammonium ions. Such salts may be prepared by methods well known in the art. All such salts are within the meaning of the term "pharmaceutically acceptable salts" as used in this specification.

The compounds of this invention may be formulated in any of a number of ways known in the art. They can be administered orally with a variety of excipients including mannitol, lactose, starch, magnesium, stearate, sodium saccharin, cellulose, magnesium carbonate, and similar compounds. They may be prepared as solutions, suspensions, tablets, pills, capsules, sustained release formulations, or powders; linked to inert supports such as beads, resins, natural or synthetic polymers, or enclosed in vesicles, micelles, or liposomes. They may also be administered in aerosol or intranasal sprays, mists or powders. If injected (intraveneously, intramuscularly, subcutaneously, intraperitoneally, or transmembranally), they may be added to water, saline, dextrose, glycerol, ethanol, or other combinations of buffer solutions. These compounds could be also be engineered for delivery by viral vectors.

It is contemplated that compound I will be administered in a dose of about 1 to 100 mg/kg/day. Preferably, compound I may be administered in a single dose or two to four divided daily doses.

DETAILED DESCRIPTION OF THE PREFERRED EMBODIMENTS

Preparation of preferred embodiments is described in further detail below. These procedures are intended to be illustrative rather than limiting.

Materials and Methods

Purification of viral cores containing endonuclease and cap-binding activities.

Influenza A/PR/8 virus (H1N1) was grown in the allantoic sacs of 10-day old embryonated eggs and isolated by differential centrifugation (12). Viral cores were prepared from 2–3 mg of whole virus by standard disruption methods (10,13) with 1.5% Triton-N101 and 10 mg/mL of lysolecithin in 100 mM Tris-HCl (pH 8.0), 100 mM KCl, 5 mM $MgCl_2$, 5% glycerol (w/v), and 1.5 mM dithiothreitol. Intact ribonucleoprotein (RNP) cores were isolated by rate-zonal centrifugation through a 30–70% (w/v) glycerol step gradient in 50 mM Tris-HCl (pH 7.8) and 150 mM NaCl, as previously described (14).

Preparation of endonuclease substrates by capping and methylation of in vitro RNA transcripts.

RNA transcripts (67-nucleotides) were prepared by in vitro run-off transcription (14) from SmaI digested pGEM-7Zf(+) plasmid DNA. Linearized plasmid DNA (5 μg) was incubated with 200 Units of SP6 RNA-polymerase (Promega), 100 Units of recombinant RNAsin (Promega) in a 50 μL reaction containing 20 mM Tris-HCl (pH 7.5), 3 mM MgCl$_2$, 1 mM spermidine, 5 mM NaCl, 10 mM dithiothreitol, and 1 mM of each ribonucleotide triphosphate (rNTP) for 2–3 hours at 37° C. Transcripts were extracted with phenol/chloroform, chromatographed through Quik-Spin G-25 columns and ethanol precipitated.

The 5' triphosphorylated ends of the RNA transcripts were converted to $^{32}$P-radiolabeled cap-1 (m$^7$G*pppGm) structures by concurrent capping and methylation reactions (25 μL) containing approximately 5 pmols RNA, 2.5 Units of mRNA guanylyltransferase/(guanine-7-)-methyltransferase/5'-triphosphatase enzyme complex (15–17) from vaccinia virus and 3 μL of the CM-Sephadex fraction of vaccinia 2'-O-methyltransferase (18,19) in 25 mM HEPES (pH 7.5), 2.5 mM MgCl$_2$, 8 mM dithiothreitol, 10 μmM GTP, 0.1 mM SAM, 5 μg RNAse-free carrier E. coli tRNA, 20 Units of recombinant RNAsin, and 50 μCi of [α-$^{32}$P] GTP (200 Ci/mmol). Concurrent capping and methylation improves the efficiency of the conversion to the cap-1 structure (11). After 1 hour of incubation at 37° C., the RNAs were phenol/chloroform extracted, spin chromatographed (Sephadex G-25), and precipitated with ethanol. Capped transcripts were further purified by electrophoresis in 15% polyacrylamide gels containing 7M urea (10). The capped 67-nucleotide transcripts were eluted by soaking gel slices overnight at 37° C. in 0.75M ammonium acetate containing 0.1 mM EDTA, 0.1% SDS, and 10 μg/mL E. coli tRNA (RNAse free), then recovered by ethanol precipitation (20).

Viral endonuclease reaction conditions.

The capped $^{32}$P-RNA was incubated with purified viral cores for 45 minutes at 31° C., in a reaction volume of 5 μL containing 200 ng viral cores, 50 mM Tris-HCl (pH 8.3), 0.25% (v/v) Triton-N101, 100 mM KCl, 5 mM MgCl$_2$, 1 mM DTT, 5 μg of E coli tRNA, and 20 Units of recombinant RNAsin (10) and terminated by the addition of 5 μL of 80% formamide containing 10% glycerol, 2.5 mM EDTA, 0.01% bromophenol blue and 0.01% xylene cyanol. For reactions that elongate the primer fragments, one or more of the rNTPs were included during the cleavage reactions or added as a chase after the initial cleavage (see Brief Description of the Figures). Reaction products were heated 2–3 minutes at 90°–95° C., separated on denaturing 20% polyacrylamide gels (19:1 acrylamide:bis) containing 7M urea (20% PAGE/7M urea) in 135 mM-Tris-45 mM borate-2.5 mM EDTA buffer, and analyzed by autoradiography.

Generation, isolation, cleavage and elongation of cap-1 containing RNA fragments.

Shorter fragments of the 67-nucleotide pGEM-7Zf(+) RNA transcript containing a common radiolabeled cap-1 structure were generated by partial digestion of the full-length capped substrate with either PhyM, T1, or CL3 RNases, followed by separation of the resulting 3'-phosphate terminated fragments on 20% PAGE/7M urea gels. Individual fragments were recovered from excised gel slices by elution and ethanol precipitation as described above. The 3'-phosphates (3'-P) were partially converted to 3'-hydroxyls (3'-OH) by incubation with T4 polynucleotide kinase in the absence of ATP (reverse reaction), for 30 minutes at 37° C., extracted with phenol/chloroform and precipitated with ethanol. These 3'-OH terminated fragments and their corresponding 3'-phosphates were then assayed in cleavage and elongation reactions as described above.

Removal and analysis of 5' cap structures.

5' caps were removed from some RNAs (21) by standard β-elimination procedure or with tobacco acid pyrophosphatase (TAP). Thin-layer chromatographic (TLC) analyses of the 5' terminal cap structures released following complete P1 RNAse digestions of pendant RNAs were done on Whatman PEI-cellulose (22). Sample Rfs were compared to authentic capped dinucleotides following development with a mobile phase consisting of 4M urea, 50 mM Tris-HCl, pH 8.0, and 200 mM NaCl.

In vitro RNA transcription assay.

Purified virus (1 μg) and 17 nM of Cap-1 AIMV were incubated for 45 minutes at 31° C., in a reaction volume of 50 μL containing 50 mM Tris-HCl, pH 7.8, 120 mM KCl, 1 mM DTT, 5 mM MgCl$_2$, 0.25% Triton-N101, 100 μM ATP, 20 μM each of CTP and GTP, 1 μM UTP, and 1 μCi of [α-$^{35}$S] UTP (20 Ci/mmol). Reaction products were applied to Whatman GF/C filters, soaked for 10 minutes in ice cold 10% TCA containing 20 mM sodium pyrophosphate, washed 3 times for 10 minutes with cold 1N HCl, once with 95% ethanol, then air-dried. Incorporated radioactivity was determined by liquid scintillation counting.

Capped RNA binding assays.

Lysed virus (2 μg) or isolated viral cores (1 μg) were incubated for 30 minutes at 31° C. with $^{35}$S-labeled VSV (23,24) mRNA (10 nM) in a 50 μL binding buffer consisting of 50 mM Tris-HCl pH 7.8, 100 mM KCl, 0.05% Triton-N101, 2 mM DTT, 1 mM EDTA, 100 μg/mL BSA (DNase and RNase-free), 100 μg/mL yeast tRNA, and 20 Units of recombinant RNasin. EDTA was included to chelate the residual Mg$^{2+}$ in the viral cores. In the filter binding assay, polymerase-mRNA complexes were collected on a vacuum filtration manifold onto 0.45 m pre-soaked nitrocellulose membrane disks (Schleicher & Schuell) at 1–2 mL/min. Samples (40 μL) were applied and immediately washed with two 650 μL aliquots of wash buffer (50 mM Tris-HCl, pH 7.8, 100 mM KCl), then filters were dried under a heat lamp and protein-bound radioactivity determined by liquid scintillation counting. In the centrifuge assay, the 50 μL binding reaction was centrifuged in a Beckman Airfuge for 90 minutes at 90,000 rpm through a 150 μL cushion of 10% glycerol, 10 mM Tris-HCl, pH 7.8, 100 mM NaCl, 1 mM EDTA. The complexes in the pellet were resuspended in appropriate buffers for liquid scintillation counting or electrophoretic analysis.

Results

Cleavage and elongation of capped synthetic substrate.

A novel 67-nucleotide RNA was synthesized from a SmaI digest of the pGEM-7Zf(+) plasmid and subsequently capped at its 5' end with radiolabeled [α-$^{32}$P]GTP. Incubation of this capped 67-nucleotide RNA (SEQ. ID. NO.: 8)

Figure 1:
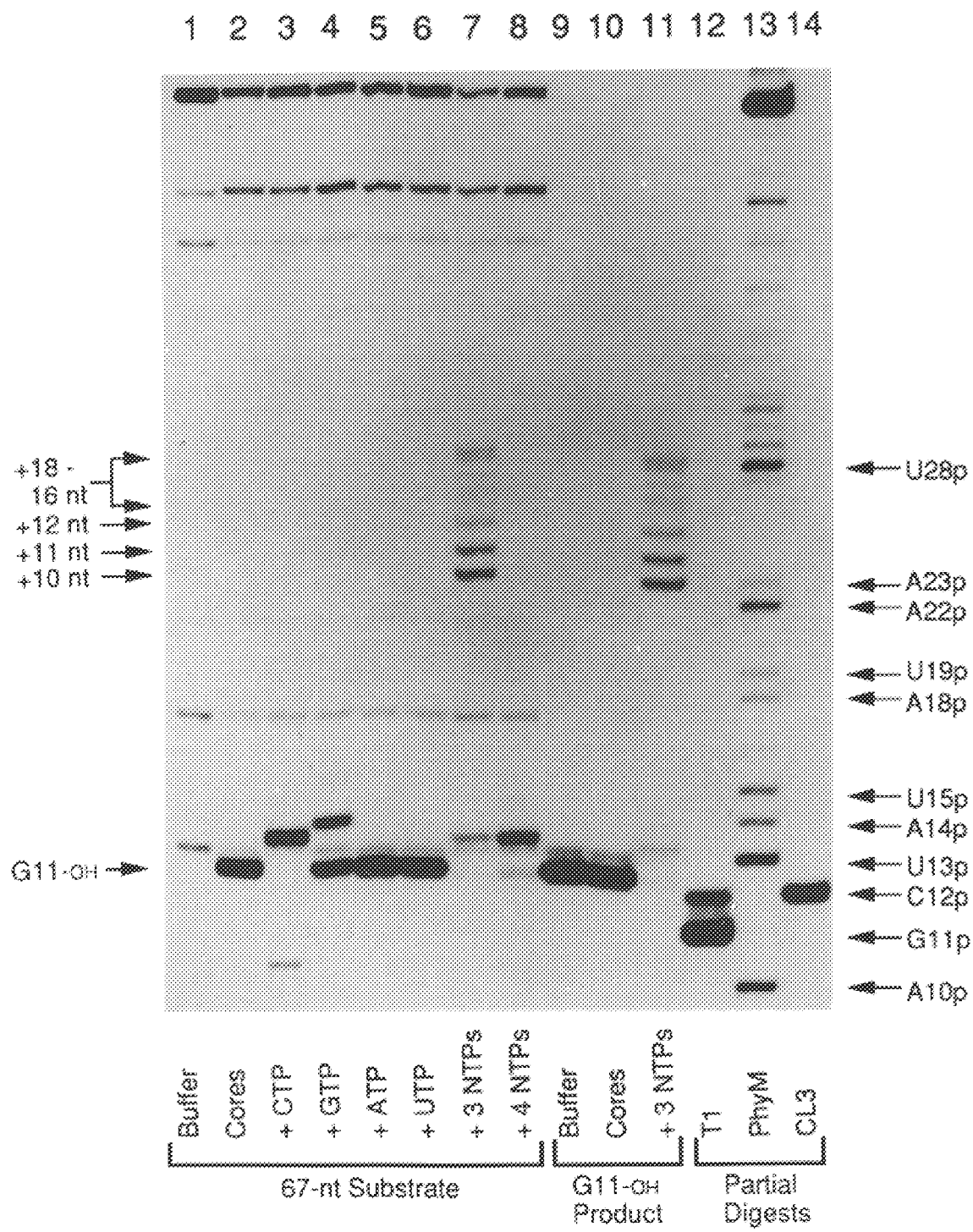
In FIG. 1, the 5' radiolabeled and capped 67-nucleotide substrate and its cleavage product function as primers for transcription. Viral cores were incubated for 45 minutes at 31° C. with the 67-nucleotide substrate in the absence (lane 2) or presence (lanes 3–8) of one or more NTPs. In addition, the G11-OH product was separately isolated from 20% PAGE/7M urea gels and similarly reacted (lanes 9-11). Elongation of the G11-OH product in the presence of ATP, CTP and GTP (3 NTP's, lanes 7 and 11) by 10, 11, 12, or 16–18 nucleotides is indicated. With all four NTPs present, elongation proceeded to yield transcripts that trailed from the origin of the gel (above the top of the autoradiogram). Digestion of the capped 67-nucleotide substrate by RNAses T1 (lane 12, GpN), PhyM (lane 13, ApN and UpN), and CL3 (lane 14, CpN) are used as markers. The migration of the G11-OH product is slower than its corresponding G11p product since it lacks the additional charge conferred by a 3'-phosphate (p) and actually co-migrates with or migrates slightly slower than the C12p fragment.

m$^7$GpppGmAAUACUCAAGCUAU(N)$_{42}$-OH with viral cores in the absence of nucleotide triphosphates (FIG. 1, lane 1) resulted in time-dependent accumulation of a single 3'-OH terminated capped 11-nucleotide fragment (SEQ. ID. NO.: 5, also listed in Table 1 and FIG. 4),

m$^7$GpppGmAAUACUCAAG-OH.

Assignment of the cleavage product was made from comparison of its migration with specific dephosphorylated fragments generated from the 67-nucleotide pGEM substrate. Cleavage was dependent on $Mg^{2+}$ and was linear for about 1 hour before leveling off.

Occasionally, additional minor cleavage products were detected, but these are non-specific as they are not $Mg^{2+}$ dependent and are found in the absence of viral cores (lane 1). These non-specific cleavages are attributed to general RNA hydrolysis of labile sites of this transcript (25) or by the presence of contaminating host-derived nucleases.

Incubation of capped 67-nucleotide transcript with viral cores in the presence of single or multiple nucleotides (FIG. 1, lanes 1–8) resulted in more slowly migrating products, depending on the identity of the nucleotides added. These results indicated that the G11-OH cleavage product could function as a primer for viral transcription. It should be noted that 3'-phosphate terminated RNA fragments migrate faster than their corresponding 3'-OH terminated ones, so that the G11-OH fragment migrated only slightly ahead of the U13-P fragment marker and behind the C12-P fragment marker. A single CMP was quantitatively added to the G11-OH product (lane 3), whereas 1–3 GMPs were efficiently added to cleaved primer (lane 4). Neither AMP nor UMP alone could be incorporated by the viral polymerase (lanes 5 and 6). These data are consistent with previous results involving nucleotide additions to G-terminated primer fragments (10,26) which can prime off the second or third bases from the 3' end of the vRNA, whereas A-terminated primers can only prime off the penultimate base. The additional G residues which may be added non-specifically (lane 4) could be related to the proofreading property associated with the viral polymerase (26). Addition of only ATP, CTP and GTP (3 NTPs) blocks transcription from each of the 8 viral genome segments at the first virally encoded UMP, with incorporation resulting in elongation of the G11-OH cleavage product by 10 (for PB2, PA, M), 11 (for NP, NS), 12 (for NA), 16 (for HA), or 17 (for PB1) nucleotides (4, 27, 28), if priming occurred off the 3rd G base of the viral template or by 11, 12, 13, 17 and 18 nucleotides if priming occurred from the penultimate C. In the presence of all four nucleotides, a band trailing from the gel origin was observed, consistent with elongation to longer transcripts which do not enter the gel. Interestingly, significant amounts of a band migrating as the cleavage product elongated by one nucleotide did not chase into fully elongated products even in the presence of 3 or 4 NTPs (lanes 7 and 8). This may be indicative of the partitioning of initiated transcription complexes between premature termination ("abortive initiation") and productive elongation, as has been noted with other RNA polymerases (25,29,30).

The cleavage products were then isolated from polyacrylamide gels and added back to cores. Incubation of the gel-purified G11-OH fragment in the cleavage/elongation reaction did not result in further cleavage (lane 10), however it was able to prime with an efficiency similar to that obtained with the full-length substrate (compare lanes 7 and 11). Thus, cleavage and elongation of this synthetic substrate could be uncoupled, as observed previously for other substrates in vitro (6,31).

Figure 2B:
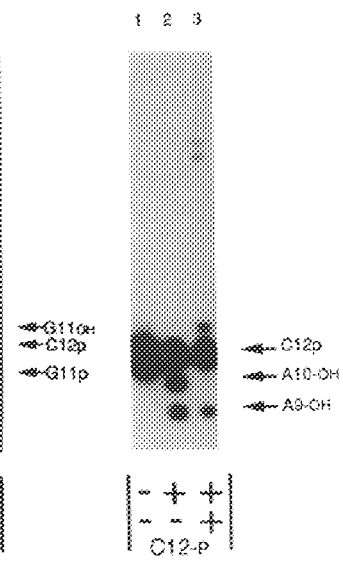

Size requirements for endonucleolytic cleavage and priming activity of RNA substrates In order to determine the shortest subset of the pGEM-7Zf(+) RNA that could be cleaved by the virion endonuclease, a panel of cap-1 containing fragments was isolated following limited RNAse digestions of the capped 67-nucleotide substrate. Digestions with RNAses T1, PhyM, and CL3 resulted in fragments that contained a 3' phosphate and a constant radiolabeled 5' cap-1 ($m^7G$*pppGm). These 3' truncated fragments enabled us to directly compare the effect of chain length on cleavage. All of the capped substrates containing RNA chains of more than 12 nucleotides were cleaved to the G11-OH fragment and primed transcription. Cleavage and elongation results for capped fragments with chains of 13 or fewer nucleotides are presented in FIG. 2A (lanes 17–19) and summarized in Table 1. The U13-P fragment (containing a 3'-phosphate) was cleaved in the absence of ribonucleotides to an 11 base primer (lane 18). When ribonucleotides ATP, GTP and CTP are added, normal elongation is observed. When the A10-P or G11-P fragments (lanes 8–13) were added to virus cores, essentially no cleavage of the 3' phosphate and little elongation of this primer could be detected (lanes 9,10,12,13). A minor amount of G11-P fragment was cleaved to the A9-OH fragment, which was inefficiently elongated (compare lanes 2,3 with 12,13). The migration of the purified C12-P fragment overlaps with the G11-OH fragment, so it could not be determined whether this cleavage occurred. However, cleavage products could be observed which correspond to A10-OH and A9-OH (FIG. 2B, lane 2). A small amount of elongation was observed when three NTPs were added (FIG. 2B, lane 3), and this appears to specifically originate from the A10-OH fragment rather than the A9-OH fragment which is inefficiently elongated as noted above. This result suggests that little cleavage of the C12-P fragment to the G11-OH fragment occurred, since this latter oligonucleotide should efficiently prime transcription.

The lack of elongation of fragments terminated in a 3' phosphate would be consistent with the general requirement of RNA polymerases for 3'-OH termini on the growing ends of polynucleotide transcripts or primers. Also, since little if any dephosphorylation of the A10-P, G11-P and C12-P is observed, the viral endonuclease does not appear to have an active 3'-phosphatase, but must directly cleave on the 5' side of a phosphodiester bond to yield a 3'-OH on the pendant nucleoside. This is similar to nuclease P1 but in contrast to the T1, T2, PhyM, and CL3 RNAses.

Figure 3A:
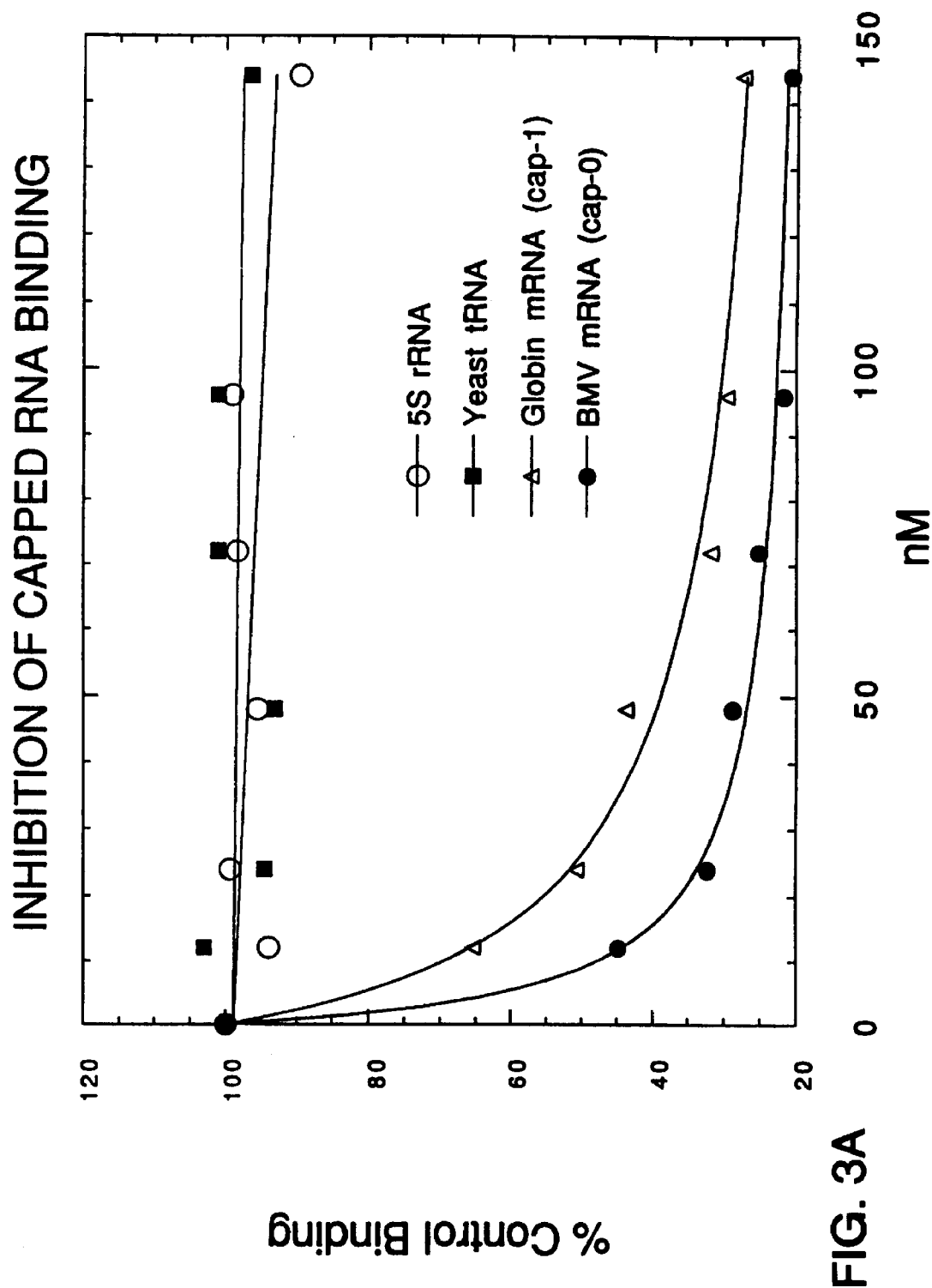
FIG. 3A–B shows inhibition of radiolabeled [$^{35}$S] cap-1 VSV mRNA binding to virus. (A) Unlabeled capped or uncapped RNAs were incubated with lysed virus in the presence of radiolabeled VSV mRNA substrate filtered through nitrocellulose membranes. The protein-bound radiolabel was determined by liquid scintillation counting. (B) Same as in (A), but with commercially available GTP, dinucleotide cap derivatives, or unlabeled cap-1 or "core" (cap-(-1), wherein X is N in compound I and $R^2$ of $N^1$ is hydroxy) capped VSV mRNA.

As the A10-P, G11-P and C12-P fragments could not be utilized through dephosphorylation by the viral polymerase, these purified oligonucleotides were enzymatically dephosphorylated with T4 polynucleotide kinase in order to ascertain the chain length requirements for primer activity. Since recovery and dephosphorylation of capped oligonucleotides of less than 11 nucleotides were inefficient, the resulting A9 and A10 products contained mixtures of phosphorylated and dephosphorylated oligonucleotides. (FIG. 3A, lanes 2–7), whereas the C12-OH fragment was gel-purified and appears as a single band (FIG. 3A, lanes 14–16). The A10-OH segment was not cleaved but directly primed elongation (FIG. 3A, lanes 5–7). The A9-OH fragment appeared to promote an abortive elongation product or primed transcription very inefficiently, as most of the product is only 2 nucleotides longer and the normal pattern of terminated fragments is absent.

The C12-OH segment also appeared to prime transcription without cleavage (lanes 14–16), although a minor amount of secondary cleavage to a putative A9-OH fragment occurred similar to that observed with the G11-P fragment (compare lanes 3, 12 and 15). Fragments that were tested with chain lengths shorter than 9 nucleotides (C8-OH, U7-OH, A5-OH, U4-OH and A3-OH) were neither cleaved nor were they able to prime transcription (Table 1). Therefore, this RNA sequence had a stringent requirement for at least 9 bases in order for the polymerase to use it as a primer.

Inhibition of binding by capped and uncapped RNAs and capped dinucleotides.

Capped mRNAs exist in various methylation states and several representative RNAs were selected to validate that the binding of cap-1 VSV mRNA to the viral polymerase was specific and cap dependent.

Figure 3B:
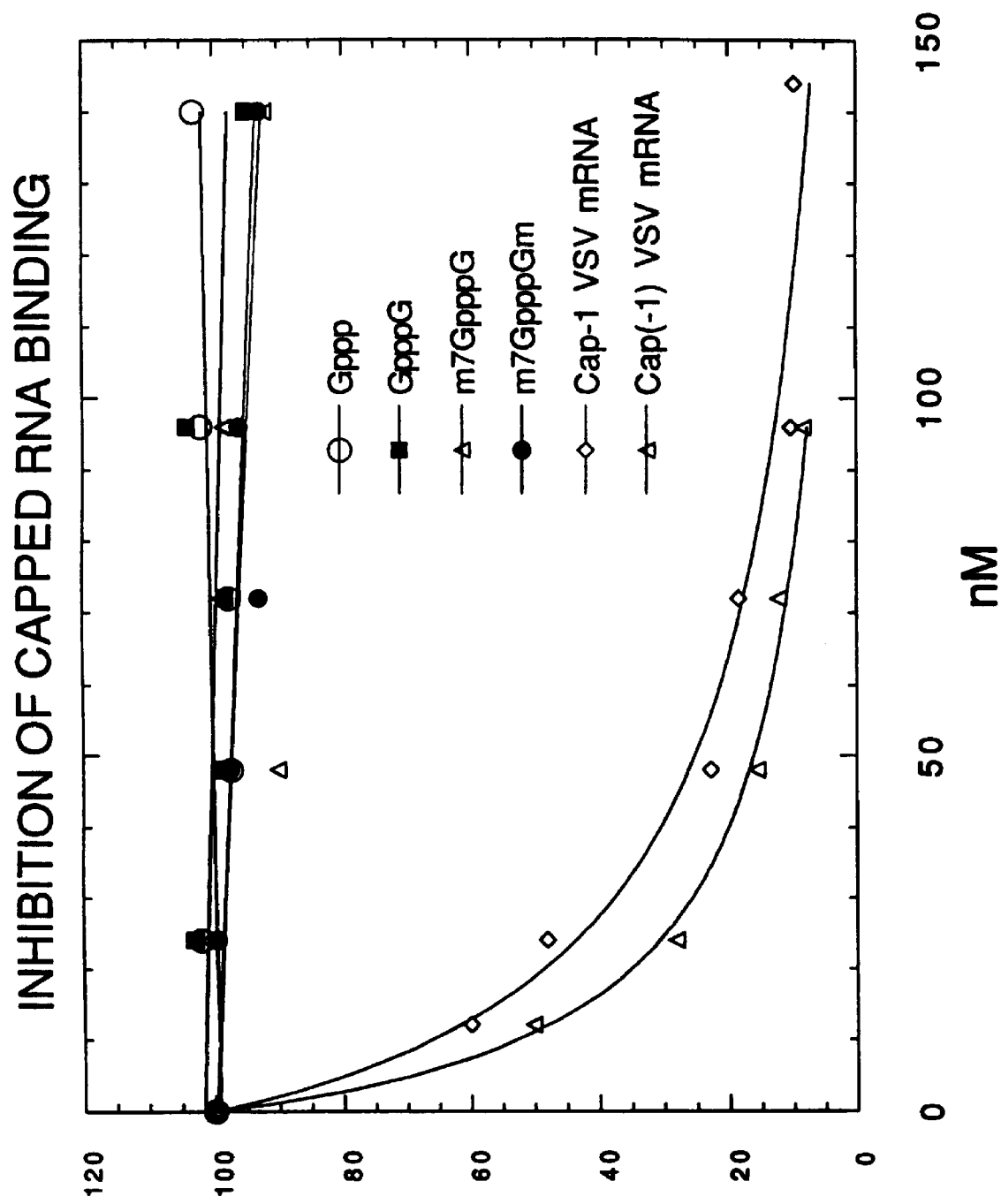

Both rabbit globin mRNA (cap-1) and BMV RNA 4 (cap-0) showed potent inhibition of the binding of cap-1 VSV mRNA to viral polymerases (FIG. 3A) with $IC_{50}$'s of 20 and 10 nM, respectively. In comparison, neither uncapped 5S ribosomal RNA (5S rRNA) nor yeast tRNA inhibited binding by more than 10% over the same 10-fold concentration range. Furthermore, the RNA component was necessary in addition to the cap for high potency inhibition (FIG. 3B) since none of the simple mono- and dinucleotide cap analogs inhibited the binding of cap-1 VSV mRNA at concentrations where the unlabeled cap-1 VSV mRNA gave potent inhibition. Interestingly, binding could also be inhibited by the "core" capped VSV mRNA which lacks the N7 methylation of the capping guanylate. However, the "core" capped VSV mRNA could not prime transcription (Table 2). Therefore, the binding measured in this system was specific and dependent upon the presence of at least the 5' G cap and a ribonucleotide component. Therefore, binding appears to only require a "core" cap structure whereas transcription has been shown previously (11) to be maximally stimulated by a cap-1 terminus. Core "cap"-containing RNAs can bind to the virion polymerase but cannot be cleaved, and thus represent another class of inhibitory oligonucleotides.

Chain length requirement for high affinity binding.

To determine how much of the ribonucleotide component was needed for capped RNA binding, a ladder of capped oligomers (left hand lane in FIG. 4) was generated by partial PhyM RNAse digestion of the 5' radiolabeled cap-1 pGEM/SmaI transcript and used as the substrate in a centrifugation assay. Influenza polymerase-RNA complexes recovered from the pellets were analyzed on 20% PAGE/7M urea gels.

Figure 4:
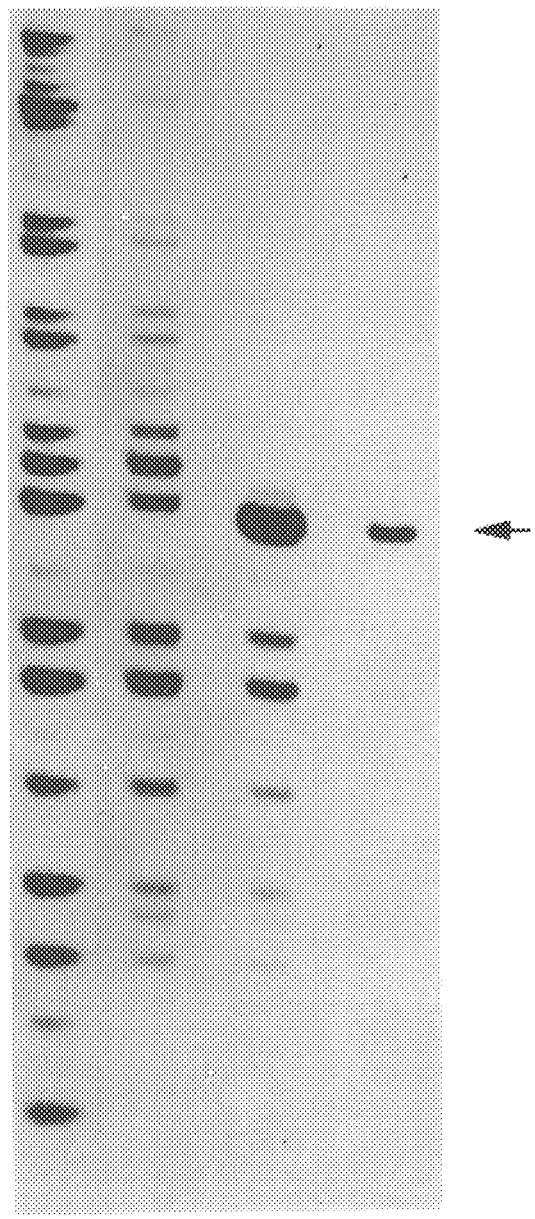
FIG. 4 shows chain length requirements for binding of capped RNA to the viral polymerase. RNA labeled at its 5' cap was partially digested with RNAse PhyM and incubated with viral cores in the presence of $MgCl_2$ (endonuclease activated) or EDTA (endonuclease inhibited). The first seven oligomers are SEQ. ID. NOS.: 1 to 7, respectively. Reactions were centrifuged through a 10% glycerol cushion, and the pellets were electrophoresed on 20% PAGE gels with 7M urea. The identities of the various bands are indicated. "Digest" is the starting material prior to incubation and ultracentrifugation.

As can be seen in FIG. 4, the smallest species that bound to the influenza polymerase was the cap dinucleotide plus three bases (chain length of 4 nucleotides). Presumably, capped RNA species larger than this also bind, though there appears to be some loss of binding of longer RNA chains longer than 14 nucleotides. The same chain length limit for binding was obtained in both the absence (middle lane) or presence of 5 mM $Mg^{2+}$. The accumulating species in the presence of $Mg^{2+}$ (endonuclease optimum) is the capped G11 endonuclease product. All the larger species have been cleaved down to this product, while those shorter have not been affected, since they exhibit band intensities similar to those seen without endonucleolytic processing.

Taken together with the cleavage elongation data above, these results show that short capped oligomers with RNA chains of more than 4 but less than 9 nucleotides attached to a capping $m^7G$ bind with relatively high affinity to the viral polymerase but cannot be further cleaved nor elongated. This chain length can be extended to 10 and 11 nucleotides if they contain 3' phosphate groups, since the viral polymerase lacks 3' dephosphatase activity. We note however, that host cell dephosphorylases could generate primers from these 10 and 11 oligonucleotides. Presumably, short "core" capped RNAs with free or dephosphorylated 3' terminii would also bind with high affinity but not be cleaved and prime transcription.

Inhibition of in vitro cap dependent transcription by short capped oligonucleotides.

Because short capped oligomers bind well to the viral polymerase site and cannot be elongated, we hypothesized that they should be potent inhibitors of primary influenza transcription. A complete T1 digest of rabbit globin mRNA yielded a pool of short capped oligomers and uncapped oligomers to test for inhibition of transcription. Since the globin mRNA (GIBCO/BRL) used is a mixture of α- and β-globin mRNAs (1:2), limited digestion with T1 RNAse which cleaves 3' to G residues is predicted to yield capped oligomers (32) with RNA chain lengths of 9 bases $m^7Gpppm^6AmCACUUCUGp$ and 7 bases $m^7Gpppm^6AmCACUUGp$, respectively. Both of these species are predicted to bind well to the viral polymerase but not be cleaved, dephosphorylated nor elongated by virtue of their short lengths and 3' phosphates. The excess of additional short uncapped RNA fragments also produced by the T1 digest are not expected to bind well nor inhibit transcription (see below).

Figure 5:
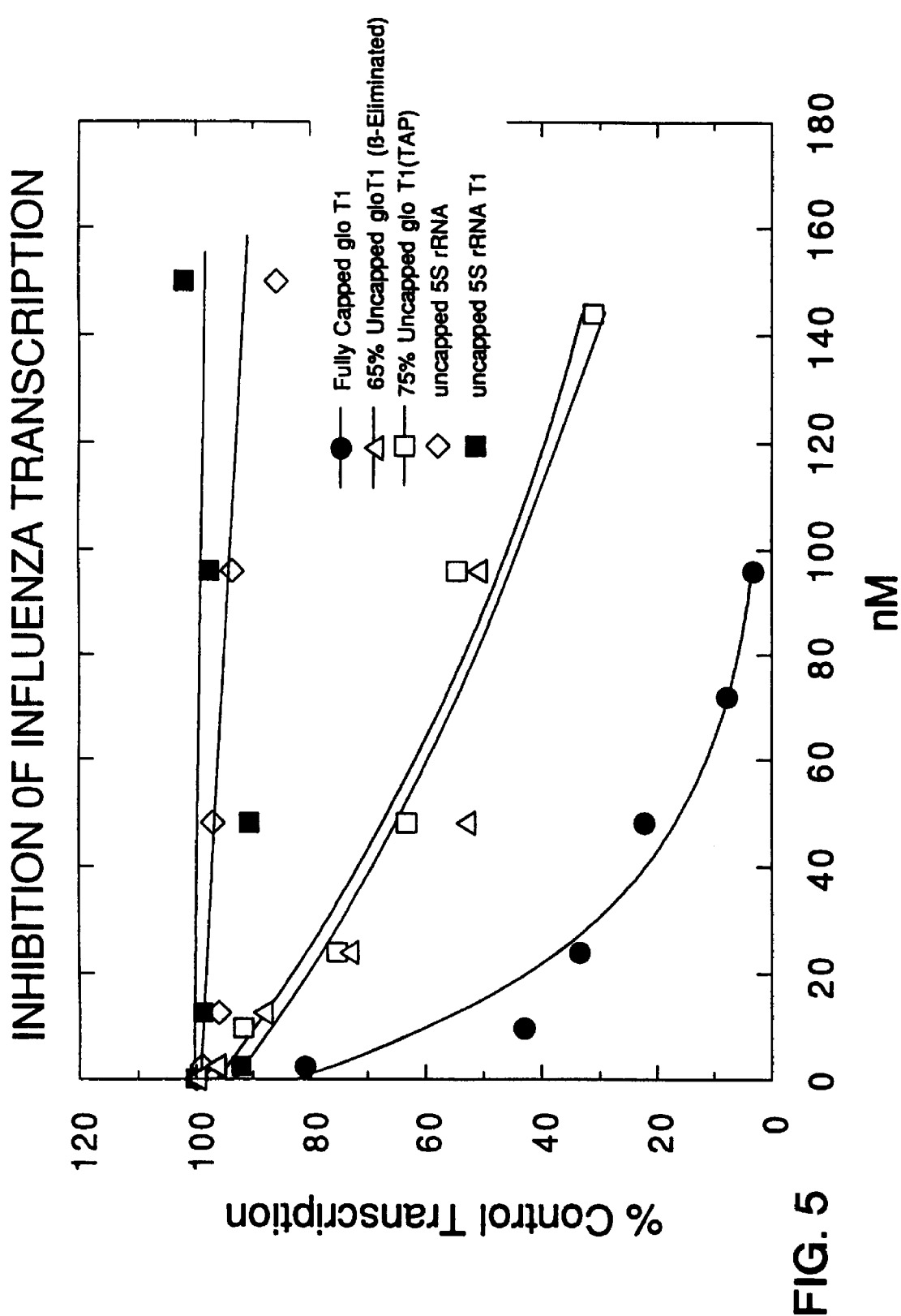
FIG. 5 shows inhibition of cap-dependent transcription. Lysed virus was incubated in a standard transcription mix (rNTPs and 35S-UTP) containing various concentrations of Ti RNAse-treated capped or uncapped RNAs. The reactions were initiated by addition of cap-1 AIMV RNA 4.

Indeed, although undigested globin mRNA is an effective primer of transcription, after complete T1 digestion it primes transcription no better than unprimed controls. As shown in FIG. 5, the complete digest of globin mRNA is an effective inhibitor of AIMV primed flu transcription with an $IC_{50}$ of 10–20 nM, similar to the $IC_{50}$ for inhibition of VSV mRNA binding by full-length globin mRNA, suggesting that these short fragments bind as well as the full-length globin.

Furthermore, removal of 5' caps by two independent methods, TAP treatment or TAP -elimination, reduced their inhibitory potencies. The decapping reactions were incomplete and the magnitude of the shift of $IC_{50}$ values to higher values could be completely accounted for by the residual percentage of capped species remaining, as ascertained by PAGE analysis (see Materials and Methods). Both uncapped 5S rRNA and T1 digested 5S rRNA did not cause any inhibition of AIMV primed transcription showing that both full-length uncapped RNAs and a pool of shorter uncapped RNAs were non-inhibitory. Therefore, both the 5' cap and the shorter RNA component were required for effective inhibition of cap-dependent transcription. Furthermore, these short capped oligomers could have cap-1, cap-0, or "core" (cap-(-1)) cap 5' termini.

TABLE 1

Activity of substrates in cleavage and elongation*

| SEQ. ID. NO. | SUBSTRATE | CLEAVAGE | ELONGATION |
|---|---|---|---|
| | 1     5     10     15 | | |
| 1 | $m^7GpppGmAAUACUCAAGCUAUGp$ | + | + |
| 2 | $m^7GpppGmAAUACUCAAGCUAUp$ | + | + |
| 3 | $m^7GpppGmAAUACUCAAGCUAp$ | + | + |
| 4 | $m^7GpppGmAAUACUCAAGCUp$ | + | + |
| 6 | $m^7GpppGmAAUACUCAAGCp$ | − | − |
| 6 | $m^7GpppGmAAUACUCAAGC$ | − | + |
| 5 | $m^7GpppGmAAUACUCAAGp$ | − | − |
| 5 | $m^7GpppGmAAUACUCAAG$ | − | + |
| 7 | $m^7GpppGmAAUACUCAAp$ | − | − |
| 7 | $m^7GpppGmAAUACUCAA$ | − | + |
| | $m^7GpppmAAUACUCAp$ | − | − |
| | $m^7GpppGmAAUACUCA$ | − | +/− |
| | $m^7GpppGmAAUACUCp$ | − | − |
| | $m^7GpppGmAAUACUC$ | − | − |
| | $m^7GpppGmAAUACUp$ | − | − |
| | $m^7GpppGmAAUACU$ | − | − |
| | $m^7GpppGmAAUACUCAAGGp$ | + | + |

TABLE 1-continued

Activity of substrates in cleavage and elongation*

| SEQ. ID. NO. | SUBSTRATE | CLEAVAGE | ELONGATION |
|---|---|---|---|

*The "+" denotes efficient elongation; "−", lack of elongation; "+/−", inefficient elongation.

TABLE 2

Capped mRNA Priming of Transcription

| mRNA primer | cpm incorporated |
|---|---|
| none | 1,993 |
| Cap-(−1) VSV | 1,701 |
| Cap-1 VSV | 16,993 |
| Cap-1 Globin | 19,820 |

Abbreviations

The abbreviations used throughout this specification are defined as follows.

| A | adenine |
|---|---|
| AIMV | alfalfa mosaic virus |
| AMP | adenosine monophosphate |
| ATP | adenosine triphosphate |
| BMV | brome mosaic virus |
| BSA | bovine serum albumin |
| CMP | cytosine monophosphate |
| C | cytosine |
| CTP | cytosine triphosphate |
| DTT | dithiothreitol |
| EDTA | ethylene diamine tetraacetic acid |
| G | guanine |
| GMP | guanosine monophosphate |
| GTP | guanosine triphosphate |
| HEPES | N-[2-hydroxyethyl]piperazine-N'-[2-ethanesulfonic acid] |
| nt | nucleotides |
| NTP | nucleotide triphosphate |
| PEI | polyethyleneimine cellulose |
| PAGE | polyacrylamide gel electrophoresis |
| RNA | ribonucleic acid |
| rNTP | ribonucleoside triphosphate |
| SAM | S-adenosyl methionine |
| TCA | trichloroacetic acid |
| tRNA | transfer RNA |
| U | uracil |
| UMP | uridine monophosphate |
| UTP | uridine triphosphate |
| vRNA | viral RNA |
| VSV | vesicular stomatitis virus |

REFERENCES

1. Krug, R. M., Alonso-Caplen, F. V., Julkunen, I., & Katze, M. G. (1989) in *The Influenza Viruses*, ed. Krug, R. M., in *The Viruses*, series eds. Fraenkel-Conrat, H. & Wagner, R. R. (Plenum Press, New York and London), pp. 89–152.
2. Blass, D., Patzelt, E., & Kuechler, E. (1982) *Virology* 116, 33–348.
3. Ulmanen, I., Broni, B. A., & Krug, R. M. (1981) *Proc. Natl. Acad. Sci. USA* 78, 7355–7359.
4. Beaton, A. R., & Krug, R. M. (1981) *Nucl. Acids Res.* 9, 4423–4436.
5. Shaw, M. W. & R. A. Lamb. (1984) *Virus Res.* 1, 455–467.
6. Braam, J., Ulmanen, I, & Krug, R. M. (1983) *Cell* 34, 609–618.
7. Kato, A., Mizumoto, K., & Ishihama, A. (1985) *Virus Res.* 3, 115–147.
8. Bouloy, M., Plotch, S. J., & Krug, R. M. (1978) *Proc. Natl. Acad. Sci. USA* 75, 4886–4890.
9. Kawakami, K., Mizumoto, M., & Ishihama, A. (1983) *Nucl. Acids Res*, 11, 3637–3649.
10. Plotch, S. J., Bouloy, M., Ulmanen, I., & Krug, R. M. (1981) *Cell* 23, 847–858.
11. Bouloy, M., Plotch S. J., & Krug, R. M. (1980) *Proc. Natl. Acad. Sci. USA* 77, 3952–3956.
12. Barrett, T., & Inglis, S. C. (1985) in *Virology A Practical Approach*, ed, Mahy, B. W. J. (IRL press, Oxford, England), pp.119–150
13. Rochavansky, O. M. (1976) *Virology* 73, 327–338.
14. Parvin, J. D., Palese, P., Honda, A., Ishihama, A., & Krystal, M. (1989) *J. Virol.* 63, 5142–5152.
15. Martin, S. A., Paoletti, E., & Moss, B. (1975) *J. Biol. Chem.* 250, 9322–9329.
16. Martin, S. A. & Moss, B. (1975) *J. Biol. Chem.* 250, 9330–9335.
17. Monroy, G., Spencer, E., & Hurwitz, H. (1978) *J. Biol. Chem.* 253, 4490–4498.
18. Barbosa, E., & Moss, B. (1978) *J. Biol Chem.* 253, 7692–7697.
19. Barbosa, E., & Moss, B (1978) *J. Biol Chem.* 253, 7698–7702.
20. Seong, B. L. & Brownlee, G. G. (1992) *Virology* 186, 247–260.
21. Schuman, S. & Moss, B. (1990) *Methods in Enzymology*, 181, 170–180.
22. Furuichi, Y. & Shatkin, A. J. (1989) *Methods in Enzymology* 180, 164–176.
23. Obijeski, J. F., Marchenko, A. T., Bishop, D. H. L., Cann, B. W., & Murphy, F. A. (1974) *J. Gen. Virol* 22, 21–23.
24. Banerjee, A. K., Moyer, S. A., & Rhodes, D. P. (1984) *Virology* 61, 547–558.
25. Surrat, C. K., Milan, S. C., & M. J. Chamberlin. (1991) *Proc. Natl. Acad. Sci. USA* 88, 7983–7987.
26. Ishihama, A., Mizumoto, K., Kawakami, K., Kato, A., & Honda, A. (1986) *J. Biol. Chem.* 261,10417–10421.
27. Robertson, J. S. (1979) *Nucl. Acids Res.* 6, 3745–3757.
28. Robertson, H. D., Dickson, E., Plotch, S. J., & Krug, R. M. (1980) *Nucl. Acids Res.* 8, 925–942.
29. Hagler, J. & Shuman, S. (1992) *J. Biol. Chem.* 267, 7644–7654.
30. Munson, L. M. & Reznikoff, W. S. (1981) *Biochemistry* 20, 2081–2085.
31. Kawakami, K., Ishihama, A., Ohtsuka, E., Tanaka, T., Takashima, H., & Ikehara, M. (1981) *J. Biochem.* 89, 1759–1768.
32. Lockard, R. E. & RajBhandary, U. L. (1976) *Cell* 9, 747–760.
33. Canton, A. J., & Roberston, J. S. (1980) *Nucl. Acids Res.* 8, 2591–2603.
34. Krug, R. M., Broni, B. A., & Bouloy, M. (1979) *Cell* 18, 329–334.
35. Plotch, S. J., Bouloy, M., & Krug, R. M. (1979) *Proc. Natl. Acad. Sci. USA* 76, 1618–1622.
36. Krug, R. M., Broni, B. A., LaFiandra, A. J., Morgan, M. A., & Shatkin, A. J. (1980) *Proc. Natl. Acad. Sci. USA* 77, 5874–5878.
37. Smith, J. C., Raper, R. H., Bell, L. D., Stebbing, N., & D. McGeoch. (1980) *Virology* 103, 245–249.
38. Rapaport, E. & Zamecnik (1975) *Proc. Natl. Acad. Sci. USA* 72, 314–317.
39. Wagner, E., Oberhauser, B., Holzner, A., Brunar, H., Issakides, G., Schaffner, G., Cotten, M., Knolimuller, M., & Noe, C. R. (1991) *Nucl. Acids Res.* 19, 5965–5971. Technical Report # 2 from Antiviral Incorporated, 4575 S. W. Research Way, Suite 200, Corvallis, Oreg. 97333.

What is claimed is:

1. A compound of the formula $$R-N^1-N^2-N^3-N^a-R^1$$

or pharmaceutically acceptable salts thereof, wherein:

R is

[structure: guanine-like base with X, ribose (HO, OH), and diphosphate group $-O-P(=O)(OH)-O-P(=O)(OH)-O-$]

X is N or $$\{-N^+-\} \atop {\phantom{x}|\phantom{x} \atop CH_3}$$

$N^a$ is $-N^4$, $-N^4-N^5$, $-N^4-N^5-N^6$, $-N^4-N^5-N^6-N^7$, or $-N^4-N^5-N^6-N^7-N^8$, $-N^4-N^5-N^6-N^7-N^8-N^9$, $-N^4-N^5-N^6-N^7-N^8-N^9-N^{10}$, or $-N^4-N^5-N^6-N^7-N^8-N^9-N^{10}-N^{11}$;

$N^1$, $N^2$, $N^3$, $N^4$, $N^5$, $N^6$, $N^7$, $N^8$, $N^9$, $N^{10}$, and $N^{11}$ are each independently

[structure: sugar ring with L, O, B, $R^2$ substituents]

or

[structure: morpholino ring with L, O, B, N-O substituents]

B is adenine, cytosine, guanine, thymine (provided $R^2$ is hydrogen), uracil (provided $R^2$ is hydroxy or methoxy), 6-methyladenine, 5-methylcytosine, or 2-methylguanine;

L is 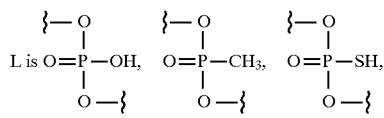

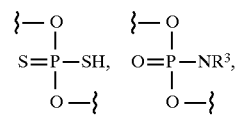

or

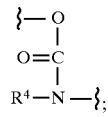

$R^1$ is hydrogen or

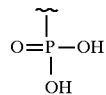

provided that $R^1$ is

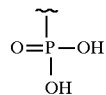

when $N^a$ is $—N^4—N^5—N^6—N^7—N^8—N^9—N^{10}$ or $—N^4—N^5—N^6—N^7—N^8—N^9—N^{10}—N^{11}$;

$R^2$ is hydrogen for each of $N^1$ to $N^{11}$ or hydroxy or methoxy for each of $N^1$ to $N^{11}$;

$R^3$ is alkyl of 1 to 4 carbon atoms; and $R^4$ is hydrogen or methyl.

2. The compound of claim 1, wherein $N^1$, $N^2$, $N^3$, $N^4$, $N^5$, $N^6$, $N^7$, $N^8$, $N^9$, $N^{10}$, and $N^{11}$ are each independently

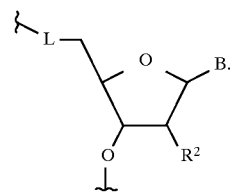

3. The compound of claim 1, wherein L is

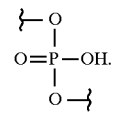

4. The compound of claim 2, wherein L is

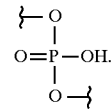

5. The compound of claim 1, wherein $N^1$ to $N^{11}$ are each independently selected from adenylate, cytidylate, guanylate, and uridylate.

6. The compound of claim 2, wherein $N^a$ is $N^4$.

7. The compound of claim 2, wherein $N^1$ is guanylate.

8. The compound of claim 2, wherein $N^2$ is adenylate.

9. The compound of claim 2, wherein $N^3$ is adenylate.

10. The compound of claim 2, wherein $N^4$ is uridylate.

11. The compound of claim 2, wherein $N^a$ is UA, UAC, UACU, UACUC, UACUCA, or UACUCA.

12. The compound of claim 2, wherein $R^1$ is

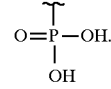

13. The compound of claim 12, wherein $N^a$ is UACUCAA or UACUCAAG.

14. The compound of claim 2 having the structure m$^7$Gpppm$^6$AmCACUUCUGp or m$^7$Gpppm$^6$AmCACUUGp.

* * * * *